United States Patent
Reah et al.

(10) Patent No.: US 12,090,062 B2
(45) Date of Patent: Sep. 17, 2024

(54) INTER VERTEBRAL DEVICES

(71) Applicant: AXIS SPINE TECHNOLOGIES LTD, St. Albans (GB)

(72) Inventors: Christopher Reah, St. Albans (GB); Jonathan Arcos, St. Albans (GB); Nicholas Sandham, London (GB); David Powell, London (GB); John Sutcliffe, Chelmsford (GB); Patrick McKenna, Stratfield Saye (GB)

(73) Assignee: AXIS SPINE TECHNOLOGIES LTD, St. Albans (GB)

( * ) Notice: Subject to any disclaimer, the term of this patent is extended or adjusted under 35 U.S.C. 154(b) by 603 days.

(21) Appl. No.: 17/294,683

(22) PCT Filed: Nov. 19, 2019

(86) PCT No.: PCT/GB2019/053275
§ 371 (c)(1),
(2) Date: May 17, 2021

(87) PCT Pub. No.: WO2020/104790
PCT Pub. Date: May 28, 2020

(65) Prior Publication Data
US 2022/0015920 A1    Jan. 20, 2022

(30) Foreign Application Priority Data
Nov. 19, 2018 (GB) ...................... 1818849

(51) Int. Cl.
*A61F 2/44* (2006.01)
*A61F 2/30* (2006.01)

(52) U.S. Cl.
CPC .... *A61F 2/447* (2013.01); *A61F 2002/30266* (2013.01); *A61F 2002/30331* (2013.01);
(Continued)

(58) Field of Classification Search
CPC ............ A61F 2/447; A61F 2002/30266; A61F 2002/30331; A61F 2002/30383; A61F 2002/30505; A61F 2002/3054
(Continued)

(56) References Cited

U.S. PATENT DOCUMENTS

| | | |
|---|---|---|
| 6,045,579 A | 4/2000 | Hochshuler et al. |
| 6,102,950 A | 8/2000 | Vaccaro |

(Continued)

FOREIGN PATENT DOCUMENTS

| | | |
|---|---|---|
| EP | 2719360 | 4/2014 |
| WO | 2013184946 | 12/2013 |
| WO | 2014093136 | 6/2014 |

OTHER PUBLICATIONS

Product Brochure "Aero-LL Lateral Lumbar Interbody and Fixation System", Stryker Spine, 2016, pp. 1-52.
(Continued)

*Primary Examiner* — Jessica Weiss
(74) *Attorney, Agent, or Firm* — LIU & LIU

(57) ABSTRACT

The present invention relates to an intervertebral fusion device (10) comprising a superior component (20), an inferior component (40) receivable in an intervertebral space between first and second vertebrae, with the core component (80) insertable between the superior and inferior components to determine a separation between the superior and inferior components. The superior, inferior components and core components comprise respective formations and profiles. The formations (54, 68) present a barrier to separation of the core from one of the inferior and superior components during insertion of the core component. The profiles guide the core component during insertion of the core component while presenting no barrier to separation from each other during its insertion. The components comprise further formations (39, 76) which present a barrier to separation of the (Continued)

components from each other once the core has been fully inserted between the inferior and superior components.

22 Claims, 5 Drawing Sheets

(52) U.S. Cl.
CPC ........... *A61F 2002/30383* (2013.01); *A61F 2002/30505* (2013.01); *A61F 2002/3054* (2013.01)

(58) Field of Classification Search
USPC ............................................ 623/17.11–17.16
See application file for complete search history.

(56) References Cited

U.S. PATENT DOCUMENTS

| | | | |
|---|---|---|---|
| 6,113,637 A | 9/2000 | Gill et al. | |
| 7,938,857 B2* | 5/2011 | Garcia-Bengochea | A61F 2/4455 623/17.11 |
| 8,308,804 B2 | 11/2012 | Krueger | |
| 8,388,686 B2 | 3/2013 | Aebi et al. | |
| 9,402,739 B2 | 8/2016 | Weiman et al. | |
| 9,526,628 B2 | 12/2016 | Krueger | |
| 9,585,765 B2 | 3/2017 | Niemiec et al. | |
| 9,801,734 B1 | 10/2017 | Stein et al. | |
| 9,987,143 B2* | 6/2018 | Robinson | A61F 2/447 |
| 10,251,758 B2* | 4/2019 | Klimek | A61F 2/30767 |
| 2002/0099444 A1* | 7/2002 | Boyd | A61F 2/4455 623/23.76 |
| 2002/0143399 A1 | 10/2002 | Sutcliffe | |
| 2003/0105528 A1* | 6/2003 | Shimp | A61F 2/28 623/901 |
| 2003/0187506 A1* | 10/2003 | Ross | A61F 2/4465 623/17.13 |
| 2004/0254644 A1* | 12/2004 | Taylor | A61F 2/4425 623/17.13 |
| 2006/0015183 A1 | 1/2006 | Gilbert et al. | |
| 2007/0270957 A1* | 11/2007 | Heinz | A61F 2/4465 623/17.11 |
| 2007/0276498 A1 | 11/2007 | Aebi et al. | |
| 2008/0294260 A1 | 11/2008 | Gray | |
| 2009/0099661 A1* | 4/2009 | Bhattacharya | A61F 2/4455 623/17.11 |
| 2011/0153020 A1 | 6/2011 | Abdelgany et al. | |
| 2011/0184522 A1* | 7/2011 | Melkent | A61F 2/447 623/17.16 |
| 2013/0006357 A1 | 1/2013 | Krueger | |
| 2013/0085573 A1 | 4/2013 | Lemoine et al. | |
| 2013/0103153 A1* | 4/2013 | Blackwell | A61F 2/4611 623/17.16 |
| 2013/0158667 A1 | 6/2013 | Tabor et al. | |
| 2015/0164494 A1 | 6/2015 | Glazer | |
| 2015/0320568 A1 | 11/2015 | Ameil et al. | |
| 2016/0116396 A1 | 4/2016 | Hunt et al. | |
| 2016/0166396 A1 | 6/2016 | McClintock | |
| 2016/0213483 A1 | 7/2016 | To et al. | |
| 2017/0239063 A1 | 8/2017 | Predick | |
| 2018/0000606 A1 | 1/2018 | Hessler et al. | |
| 2018/0036141 A1 | 2/2018 | O'Neil et al. | |
| 2018/0098860 A1 | 4/2018 | To et al. | |
| 2018/0256357 A1 | 9/2018 | To et al. | |

OTHER PUBLICATIONS

International Search Report of Counterpart PCT International Application No. PCT/GB2019/053273.
International Search Report of Counterpart PCT International Application No. PCT/GB2019/053275.
International Search Report of Counterpart PCT International Application No. PCT/GB2019/053277.

* cited by examiner

INTER VERTEBRAL DEVICES

FIELD OF THE INVENTION

The present invention relates to intervertebral devices and more specifically to intervertebral fusion devices.

BACKGROUND TO THE INVENTION

Adjacent vertebrae in the spinal column are coupled to each other by an intervertebral disc. The intervertebral disc holds the adjacent vertebrae together and functions as a cushion between the vertebrae whilst allowing for relative movement of the vertebrae. Problems with intervertebral discs arise from one or more of a range of diseases and conditions. A surgical procedure, such as spinal fusion, may be used to address such problems. A typical spinal fusion procedure involves partial or full removal of a problematic intervertebral disc and installation of an intervertebral device in the place of the partially or fully removed intervertebral disc.

Known intervertebral devices are of varied form and function. Many known intervertebral devices are configured to provide for adjustment of height and functional spine unit angle to address differing extents of removal of an intervertebral disc, differing anatomy and spinal deformity. Furthermore, ease of assembly, installation, including reduced impaction loads during insertion, and disassembly are design objects for known intervertebral devices aside from issues of manufacturability and cost. Some known intervertebral devices are characterised by their complexity with such complexity being liable to result in compromise on ease of assembly, installation and disassembly, in compromise on long-term reliability, or in risk to the patient, such as from wear of material from the intervertebral device over time and loss of spinal correction.

The present inventors have become appreciative of shortcomings of known intervertebral devices, such as the shortcomings mentioned above. The present invention has been devised in light of the inventors' appreciation of such shortcomings. It is therefore an object for the present invention to provide an improved intervertebral device and more specifically an improved intervertebral fusion device. It is a further object for the present invention to provide an improved method of installing an intervertebral device in an intervertebral space between first and second adjacent vertebrae and more specifically an improved method of installing an intervertebral fusion device.

STATEMENT OF INVENTION

According to a first aspect of the present invention there is provided an intervertebral fusion device comprising:
  a superior component having a superior component top side and a superior component bottom side, the superior component being configured to be received in an intervertebral space between first and second vertebrae whereby the superior component top side abuts against the first vertebra;
  an inferior component having an inferior component top side and an inferior component bottom side, the inferior component being configured to be received in the intervertebral space between the first and second vertebrae whereby the inferior component bottom side abuts against the second vertebra, the superior component bottom side and the inferior component top side opposing each other when the superior and inferior components are received in the intervertebral space; and
  a core component configured for insertion between the superior and inferior components whereby a separation between the superior and inferior components is determined when the intervertebral fusion device is in the intervertebral space, wherein
  the core component comprises a first core formation and one of the inferior component top side and the superior component bottom side comprises a first component formation, the first core formation inter-engaging with the first component formation to present a barrier to separation of the core component and the corresponding one of the inferior and superior components from each other during insertion of the core component,
  the core component comprises a core profile and the other of the inferior component top side and the superior component bottom side comprises a component profile, the core profile and the component profile cooperating with each other during insertion of the core component to thereby guide the core component, there being no barrier to separation of the core component and the corresponding one of the inferior and superior components from each other during insertion of the core component, and
  the core component comprises a second core formation and the other of inferior component top side and the superior component bottom side comprises a second component formation, the second core formation inter-engaging with the second component formation to present a barrier to separation of the core component and the corresponding one of the inferior and superior components from each other when the core component is fully received between the inferior and superior components.

The intervertebral fusion device comprises three main components, namely a superior component, an inferior component and a core component. In use, the superior and inferior components are placed in an intervertebral space between first and second vertebrae formed by at least partial removal of a problematic intervertebral disc. The superior component has a superior component top side and a superior component bottom side with the superior component being placed in the intervertebral space such that the superior component top side faces the first vertebra or what might remain of a partially removed intervertebral disc. The inferior component has an inferior component top side and an inferior component bottom side with the inferior component being placed in the intervertebral space such that the inferior component bottom side faces the second vertebra or what might remain of a partially removed intervertebral disc. The superior component bottom side and the inferior component top side oppose each other when the superior and inferior components are received in the intervertebral space. The superior and inferior components may be in registration with each other when in the intervertebral space and more specifically when the core component is fully inserted between the superior and inferior components as described below.

The core component is configured for insertion between the superior and inferior components. In use, the core component may be inserted between the superior and inferior components when the superior and inferior components have been placed in the intervertebral space, as described above. Upon insertion the core component determines a separation between the superior and inferior components and hence a height of the intervertebral fusion device with the superior component top side abutting against the first vertebra or what remains of the partially removed intervertebral disc and with the inferior component bottom side abutting against the second vertebra or what remains of the partially removed intervertebral disc. Differing heights of intervertebral fusion device may be provided by selection from plural core components of different height.

The core component comprises a first core formation and one of the inferior component top side and the superior component bottom side comprises a first component formation. The first core formation inter-engages with the first component formation to present a barrier to separation of the core component and the corresponding one of the inferior and superior components from each other during insertion of the core component. The barrier to separation may be presented in a separation direction that extends between the inferior and superior components. Inter-engagement of the first core formation with the first component formation may provide for and maintain proper relative location of the core component and the corresponding one of the inferior and superior components in the separation direction during insertion of the core component. An extent to which the corresponding one of the inferior and superior components may move away from the core component in the separation direction may thus be limited during insertion of the core.

The core component also comprises a core profile and the other of the inferior component top side and the superior component bottom side comprises a component profile. The core profile and the component profile cooperate with each other during insertion of the core component to thereby guide the core component. During insertion of the core component, there is no barrier to separation of the core component and the corresponding one of the inferior and superior components from each other. The lack of barrier means the corresponding one of the inferior and superior components may move away from and towards the core component during insertion of the core component. Allowing for such movement of the core component away from and towards the corresponding one of the inferior and superior components may provide for ease of initial insertion of the core component, such as by way of reduced insertion load, and may allow for the position of the corresponding one of the inferior and superior components to settle in relation to the core component as insertion progresses.

The core component also comprises a second core formation and the other of inferior component top side and the superior component bottom side comprises a second component formation. The second core formation inter-engages with the second component formation to present a barrier to separation of the core component and the corresponding one of the inferior and superior components from each other when the core component is fully received between the inferior and superior components. The corresponding one of the inferior and superior components and the core component are thus held in relation to each other when the core component is fully received between the inferior and superior components. The core component may be fully received between the inferior and superior components when the core component abuts against a posterior surface of at least one of the inferior and superior components. As described above, the core profile and the component profile may cooperate with each other during insertion of the core component to guide the core component. The lack of barrier allows for the position of the corresponding one of the inferior and superior components to settle in relation to the core component as insertion progresses. When the position of the corresponding one of the inferior and superior components has settled in relation to the core component and the core is fully inserted, the barrier presented by inter-engagement of the second core formation and the second component formation presents a barrier to separation of the core component and the corresponding one of the inferior and superior components from each other.

The first core formation may be an inferior core formation and the first component formation may be an inferior component formation comprised in the inferior component top side. The barrier to separation may therefore be presented in respect of the core component and the inferior component. Furthermore, the core profile may be a superior core profile and the component profile may be a superior component profile comprised in the superior component bottom side. The lack of barrier to separation may therefore be in respect of the core component and the superior component. Having the intervertebral fusion device configured in this fashion may mean that the inferior component and core component are held together by virtue of the barrier to separation to thereby provide a firm foundation on which the intervertebral fusion device is assembled by affording more freedom of movement to the superior component during insertion of the core component.

The core component may have an upper side and a lower side. When the core component is inserted between the inferior and superior components, the upper side may face the superior component bottom side and the lower side may face the inferior component top side. The upper side and the lower side of the core component may be inclined to each other. The core component may therefore have the form of a wedge. Having the superior component profile and the superior core profile cooperate with each other with there being no resistance to separation of the core component and the superior component from each other whilst the inferior core formation inter-engages with the inferior component formation allows a wedge-shaped core component to be inserted between the inferior and superior components.

The upper side and the lower side of the core component may not meet at an acute angle whereby the core component has the form of a frustum of a wedge. The core component and the inferior and superior components may be configured for insertion of the core component to be led by the thinner edge of the thinner and thicker edges of the core component. An inclination of the inferior and superior components relative to each other may thus be determined by way of the core component further to a separation between the inferior and superior components. Extent of inclination of the inferior and superior components may be determined by selection from a plurality of core components having upper and lower sides of different relative inclinations.

One of the inferior component formation and the inferior core formation may define a groove and the other of the inferior component formation and the inferior core formation may define an elongate protrusion, the elongate protrusion being shaped to be slidably received in the groove. The elongate protrusion may be a friction fit in the groove. The groove and the elongate protrusion may extend between anterior and posterior aspects of the intervertebral fusion device. The inferior component formation may define the groove and the inferior core formation may define the elongate protrusion. Inter-engagement of groove and elongate protrusion present the barrier to separation as the core is inserted.

The inferior core formation may extend along the core component from a location on the core component spaced apart from an edge of the core component which leads insertion of the core component between the inferior and superior components. For example, and where the core component is wedge-shaped, the inferior core formation may extend along the core component from a location on the core component spaced apart from the thinner edge of the core component. Having the inferior core formation extend along the core component from a location on the core component spaced apart from the thinner edge allows the edge to be inserted first between the inferior and superior components and for the core component to be moved in the separation direction, i.e. the direction extending between the inferior and superior components, during a first stage of insertion before the inferior core formation and the inferior component formation inter-engage during a second stage of insertion. Allowing for freedom of movement in the separation direction during the first stage of insertion provides for ease of initial insertion of core component. For example, the edge of the core component may be inserted between the inferior and superior components with no great precision of positioning before the core component is pressed down against the inferior component as the core component is inserted further.

A leading edge of the core component, for example the thinner edge when the core component is wedge shaped, may have rounded corners. Such a radius on each corner of the leading edge may provide for ease of insertion of the core component between the inferior and superior components.

The inferior core formation may extend along the core component between the anterior and posterior aspects of the core component. Alternatively, the inferior core formation may extend along the core component for less than the span of the core component between the anterior and posterior aspects. The inferior core formation may extend along the core component starting from a location spaced apart from the leading edge of the core component by at least a quarter and more specifically at least a third of a distance between the leading edge and the opposite edge of the core component. In a particular form, the location may be spaced apart from the leading edge by about half of the distance between the leading edge and the opposite edge of the core component. The inferior core formation may extend along the core component from the starting location to the opposite edge of the core component.

The inferior component may comprise a first inferior component formation and a second inferior component formation, the first and second inferior component formations being towards opposite edges of the inferior component and being spaced apart in a direction transverse to the direction of insertion of the core component between the inferior and superior components. The core component may be received between the first and second inferior component formations during insertion. The first and second inferior component formations may therefore oppose each other. The core component may have first and second lateral sides which each face in a direction orthogonal to a direction of insertion of the core component and to a direction of separation of the inferior and superior components, with the first and second lateral sides facing in opposite directions. A first inferior core formation may be on the first lateral side and a second inferior core formation may be on the second lateral side. The first inferior component formation and the first inferior core formation may cooperate and the second inferior component formation and the second inferior core formation may cooperate to limit movement of the core component relative to the inferior component in the transverse direction. More specifically, the inferior component formations and the inferior core formations may provide a snug fit for the core component in the transverse direction.

The superior component may comprise a first superior component profile and a second superior component profile, the first and second superior component profiles being towards opposite edges of the superior component and being spaced apart in a direction transverse to the direction of insertion of the core component between the inferior and superior components. The core component may be received between the first and second superior component profiles during insertion. The first and second superior component profiles may therefore oppose each other. A first superior core profile may be on the first lateral side of the core component and a second superior core profile may be on the second lateral side of the core component. The first superior component profile and the first superior core profile may cooperate and the second superior component profile and the second superior core profile may cooperate to limit movement of the core component relative to the superior component in the transverse direction. More specifically, the superior component profiles and the superior core profiles may provide a snug fit for the core component in the transverse direction. As described above, there may be no barrier presented to separation of the superior component and the core component from each other. The superior component may therefore rise and fall in relation to the core component as insertion of the core component is guided by the superior component profiles and the superior core profiles.

The inferior component may comprise an inferior component rear formation which extends along a posterior aspect of the inferior component in a direction transverse to the direction of insertion of the core component. The posterior aspect is opposite the edge at which the core component is first received upon insertion. The core component may comprise an inferior core rear formation which extends along an edge of the core component which is first received between the inferior and superior components during insertion of the core component. The inferior component rear formation and the inferior core rear formation may inter-engage when the core component is fully received between the inferior and superior components to present a barrier to separation of the core component and the inferior component from each other in the separation direction. A leading edge of the core component, i.e. the edge first received between the inferior and superior components during insertion, may thus be secured against lifting away from the inferior component when the core component is fully inserted.

When the core component is fully inserted between the inferior and superior components it may be desirable to maintain the core component against ejection from between the inferior and superior components, i.e. movement of the core component in an opposite direction to the direction of insertion. The intervertebral fusion device may therefore comprise a locking arrangement, a first locking part being comprised in the core component and a second locking part being comprised in the inferior component, the first and second locking parts inter-engaging to present a barrier to ejection of the core component from between the inferior and superior components. The first locking part may comprise a living hinge which defines a protrusion thereon and the second locking part may define an aperture. The living hinge may be urged by inherent spring bias in a direction of separation of the inferior and superior components and such that that the protrusion on the living hinge is received in the aperture of the second locking part.

The second component formation may be a superior component rear formation comprised in the superior component. The superior component rear formation may extend along a posterior aspect of the superior component in a direction transverse to the direction of insertion of the core component. The posterior aspect is opposite the edge at which the core component is first received upon insertion. The second core formation may be a superior core rear formation comprised in the core component. The superior core rear formation may extend along an edge of the core component which is first received between the inferior and superior components during insertion of the core component. As described above in respect of the second component formation and the second core formation, the superior component rear formation and the superior core rear formation inter-engage when the core component is fully inserted to present a barrier to separation of the core component and superior component. As described above, the superior component profile and the superior core profile cooperate with each other to present no resistance to separation of the core component and the superior component from each other in the separation direction during insertion of the core component. The superior component rear formation and the superior core rear formation thus present a barrier to separation when the core component is fully inserted, for example when the core component abuts against a posterior surface of at least one of the inferior and superior components.

The superior component rear formation and the superior core rear formation may be configured such that they start to engage when the core component is at least 80% and more specifically at least 90% inserted between the inferior and superior components. The superior component rear formation and the superior core rear formation may be configured by their extension away from the posterior aspect towards the anterior aspect.

The superior component rear formation may comprise a first protrusion and the superior core rear formation may comprise a second protrusion, the second protrusion being received on the core component side of the first protrusion when the core component is fully inserted. Furthermore, the superior component rear formation and the superior core rear formation may be shaped to draw the superior component and the core component progressively closer together during a last stage of insertion of the core component. As mentioned above, the superior component rear formation and the superior core rear formation may start to inter-engage when the core component is at least 80% inserted. Each of the first and second protrusions may define an inclined surface, the two inclined surfaces sliding over each other to draw the superior component and the core component progressively closer together.

The second component formation may be a superior component front formation comprised in the superior component. The superior component front formation may be towards an edge of the superior component at which the core component is first received upon insertion of the core component. The second core formation may be a superior core front formation comprised in the core component. The superior core front formation may be towards an edge of the core component opposite the edge first received between the inferior and superior components during insertion of the core component. The superior component front formation and the superior core front formation may inter-engage when the core component is fully inserted to present a barrier to separation of the core component and superior component in the separation direction. The superior component front formation and the superior core front formation may inter-engage and the superior component rear formation and the superior core rear formation may also inter-engage to present barriers to separation at opposite edges of the core component. The superior component front formation and the superior core front formation, and the superior component rear formation and the superior core rear formation may be operative to stop the superior component lifting or at least limit an extent to which the superior component can lift from the core component.

The superior component front formation may comprise a recess and the superior core rear formation may comprise a protrusion, the protrusion being received on the recess when the core component is fully inserted. Furthermore, the superior component front formation and the superior core front formation may be shaped to draw the superior component and the core component progressively closer together during a last stage of insertion of the core component. Each of the superior component front formation and the superior core front formation may define an inclined surface, the two inclined surfaces sliding over each other to draw the superior component and the core component progressively closer together. The superior component front formation and the superior core front formation may start to inter-engage with each other at a same extent of insertion of the core component as when the superior component rear formation and the superior core rear formation start to inter-engage with each other. Opposite edges of the core component are thus drawn towards the superior component simultaneously as the core component is inserted.

References herein to anterior or to anterior aspect are to the anterior aspect of the intervertebral fusion device itself and not to the anterior aspect of the patient. The anterior aspect of the intervertebral fusion device itself therefore means the aspect at which the core component is inserted between the superior and inferior components. Correspondingly, references herein to posterior or to posterior aspect are to the posterior aspect of the intervertebral fusion device itself and not to the posterior aspect of the patient. The anterior and posterior aspects are oppositely directed. The intervertebral fusion device may be an anterior, anterior oblique, lateral or direct lateral intervertebral fusion device.

The superior component, the inferior component and the core component may be separate components. Furthermore, the superior component and the inferior component may be disconnected from each other in the absence of the core component. Having separate inferior and superior components and core component and more specifically disconnected inferior and superior components means that the components may be introduced to the intervertebral space more gently compared with known single piece intervertebral fusion devices which often need to be hammered into place. Such a less gentle insertion process may damage the intervertebral fusion device, may increase time required for the intervertebral fusion device to settle in the intervertebral space, and may result in trauma to vertebral bodies, adjacent soft tissues including neural structures. On the subject of trauma, a device that is hammered into place is liable to create microfractures in the vertebrae which could lead to subsidence of the device into the host bone. Furthermore, having separate components and in particular a core component separate to the inferior and superior components allows for differences in dimensions of intervertebral spaces, differences in angle between the adjacent vertebrae that define the intervertebral space, and degree of spinal alignment and/or correction. Each of the superior component, the inferior component and the core component may be integrally formed. The superior component and the inferior component may not engage with each other, other than by way of the core component.

Each of the inferior and superior components may have the form of a plate, albeit a plate having structures thereon that provide for mechanical engagement with the core component, whereby it is thin relative to its length and width. At least one of the superior component top side and the inferior component bottom side may be shaped in the coronal or sagittal planes, for example domed, to enhance fit and contact with the adjacent vertebrae.

At least one of the superior component top side and the inferior component bottom side may be configured to provide for fusion. For example, the top or bottom side may comprise formations, such as protrusions, which, in use, engage with the bone of the vertebra. By way of another example, the top and/or bottom side may define apertures for passage of bone graft material therethrough from an interior of the intervertebral fusion device. By way of a further example, the top or bottom side may have a coating thereon or impregnation therein. The coating or impregnation may comprise material that provides for bone adhesion and/or bone formation to encourage bone to grow up to and bond onto the intervertebral fusion device to thereby provide long term stable attachment. One or more known coatings may be used, such as porous mesh, tricalcium phosphate (TCP), hydroxyapatite (HA) or bone morphogenetic protein (BMP).

At least one of the superior component, the core component and the inferior component may be formed from a metal, such as titanium, or a metal alloy, such as stainless steel, Ti6Al4V, CoCr or nitinol. Nitinol may be useful in respect of cooperating parts of the superior component, the core component and the inferior component. At least one of the superior component, the core component and the inferior component may be formed from a plastics material and more specifically a thermoplastic polymer, such as PEEK or carbon reinforced PEEK. In forms of the invention, the core component may be formed by 3D printing whereby the core component has the form of a 3D lattice. The aforementioned materials may be used to form the core component by way of 3D printing.

When assembled, the intervertebral fusion device may have a range of length by width from 20 mm by 15 mm to 65 mm by 50 mm. Where there is an oblique intervertebral fusion device, the range of length by width may be from 20 mm by 15 mm to 40 mm by 35 mm. Where there is an anterior intervertebral fusion device, the range of length by width may be from 20 mm by 20 mm to 50 mm by 50 mm. Where there is a lateral intervertebral fusion device, the range of length by width may be from 40 mm by 18 mm to 65 mm by 40 mm. A height of the intervertebral fusion device may be 5 mm to 15 mm at the posterior aspect.

According to a second aspect of the present invention there is provided a method of installing an intervertebral fusion device in an intervertebral space between first and second adjacent vertebrae, the intervertebral fusion device comprising a superior component having a superior component top side and a superior component bottom side, an inferior component having an inferior component top side and an inferior component bottom side, and a core component, the method comprising:

positioning the superior component and the inferior component relative to each other such that the superior component bottom side and the inferior component top side oppose each other;

inserting the core component between the superior and inferior components whereby a separation between the superior and inferior components is determined; and disposing the intervertebral fusion device in the intervertebral space such that the superior component top side abuts against the first vertebra and the inferior component bottom side abuts against the second vertebra, wherein the core component comprises a first core formation and one of the inferior component top side and the superior component bottom side comprises a first component formation, the first core formation inter-engaging with the first component formation to present a barrier to separation of the core component and the corresponding one of the inferior and superior components from each other during insertion of the core component, wherein the core component comprises a core profile and the other of the inferior component top side and the superior component bottom side comprises a component profile, the core profile and the component profile cooperating with each other during insertion of the core component to thereby guide the core component, there being no barrier to separation of the core component and the corresponding one of the inferior and superior components from each other during insertion of the core component, and wherein the core component comprises a second core formation and the other of inferior component top side and the superior component bottom side comprises a second component formation, the second core formation inter-engaging with the second component formation to present a barrier to separation of the core component and the corresponding one of the inferior and superior components from each other when the core component is fully received between the inferior and superior components.

The intervertebral fusion device may be installed in an intervertebral space by positioning the superior component and the inferior component relative to each other in the intervertebral space before the core component is inserted between the superior and inferior components. Alternatively, the intervertebral fusion device may be installed in an intervertebral space by positioning the superior component and the inferior component relative to each other at a location apart from the intervertebral space and inserting the core component between the superior and inferior components at this location before the thus assembled intervertebral fusion device is installed in the intervertebral space.

Further embodiments of the second aspect of the present invention may comprise one or more features of the first aspect of the present invention.

BRIEF DESCRIPTION OF DRAWINGS

The present invention will now be described by way of example only with reference to the following drawings, of which.

DESCRIPTION OF EMBODIMENTS

Figure 1A:
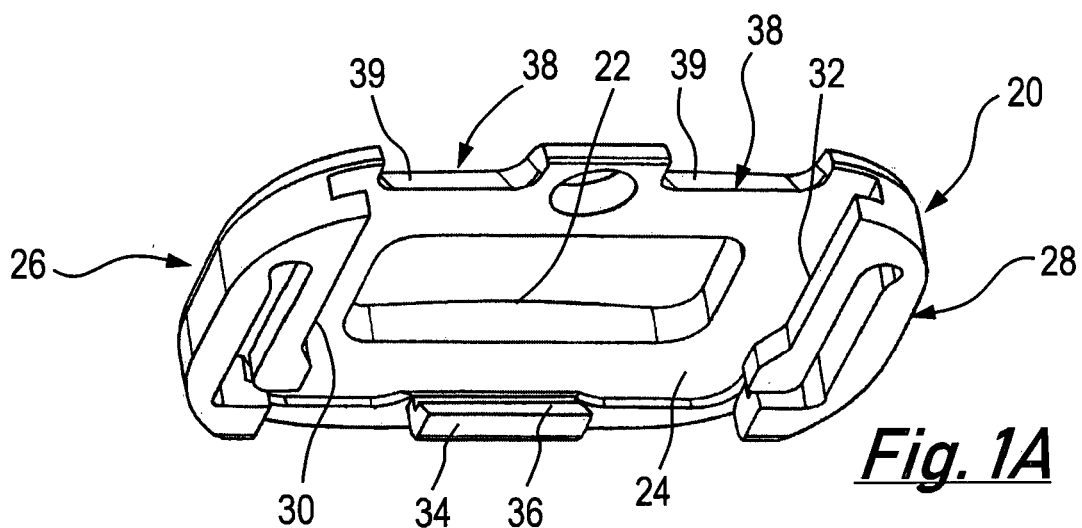
FIG. 1A shows a superior component of a first embodiment of the present invention.
Figure 1B:
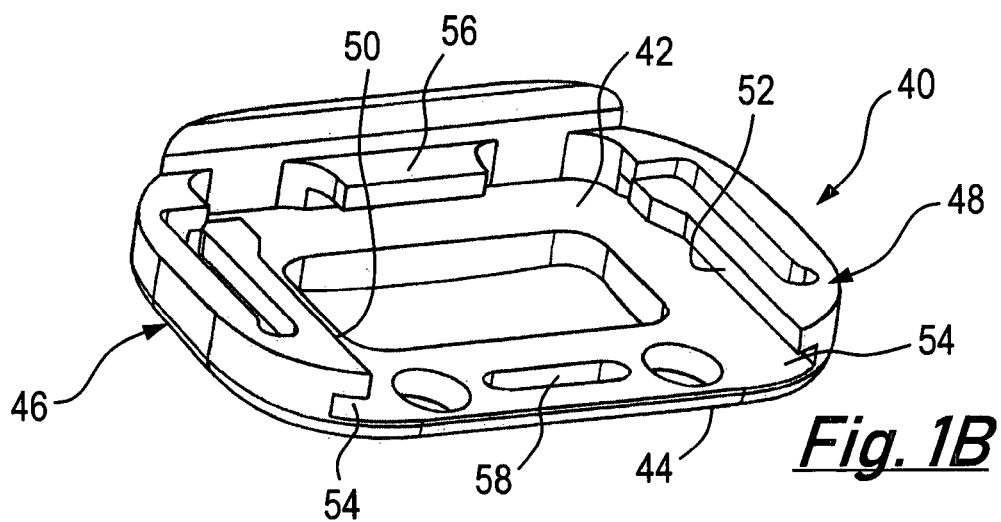
FIG. 1B shows an inferior component of the first embodiment of the present invention.
Figure 1C:
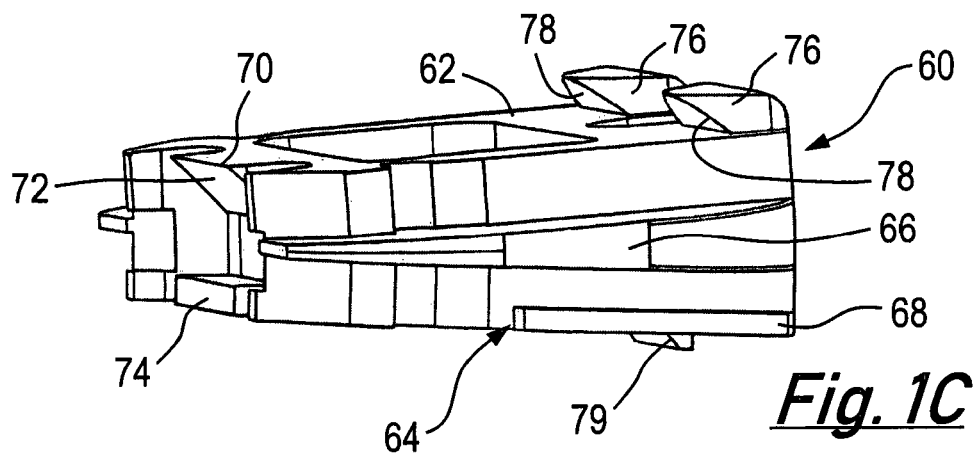
FIG. 1C shows core component of the first embodiment of the present invention.
Figure 2A:
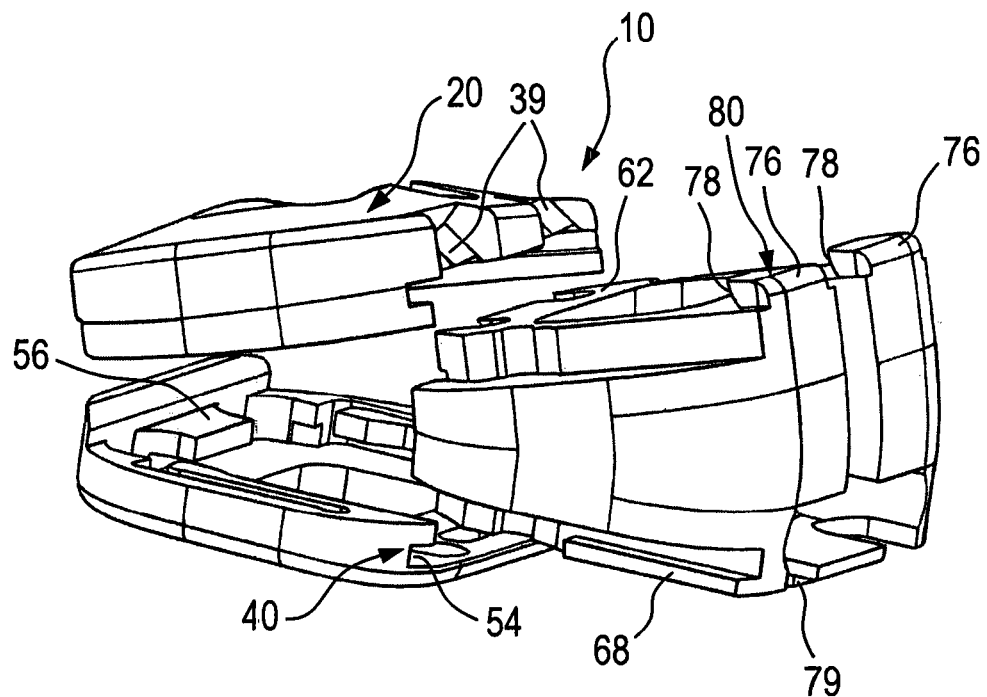
FIG. 2A shows the core component before insertion between the superior and inferior components according to a second embodiment.
Figure 2B:
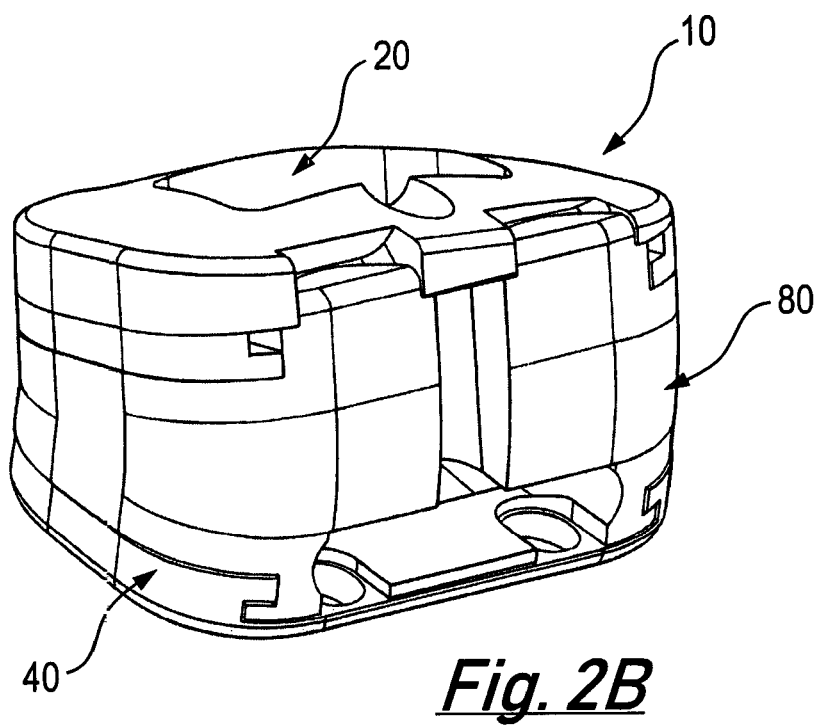
FIG. 2B shows the core component after insertion between the superior and inferior components according to the second embodiment.
Figure 3A:
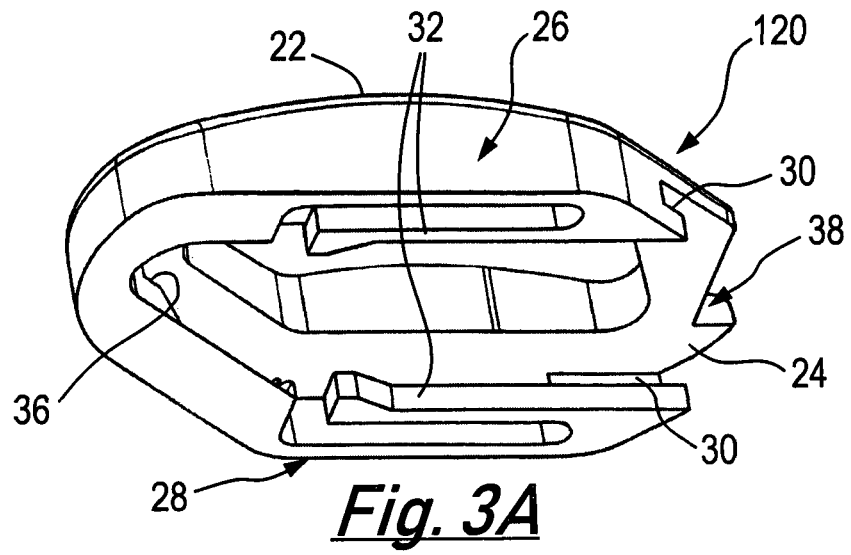
FIG. 3A shows a superior component of a third embodiment of the present invention.
Figure 3B:
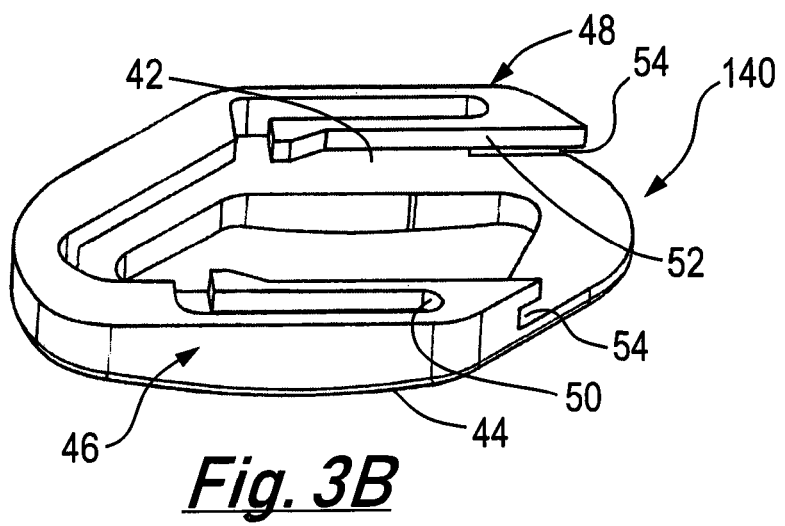
FIG. 3B shows an inferior component of the third embodiment of the present invention.
Figure 3C:
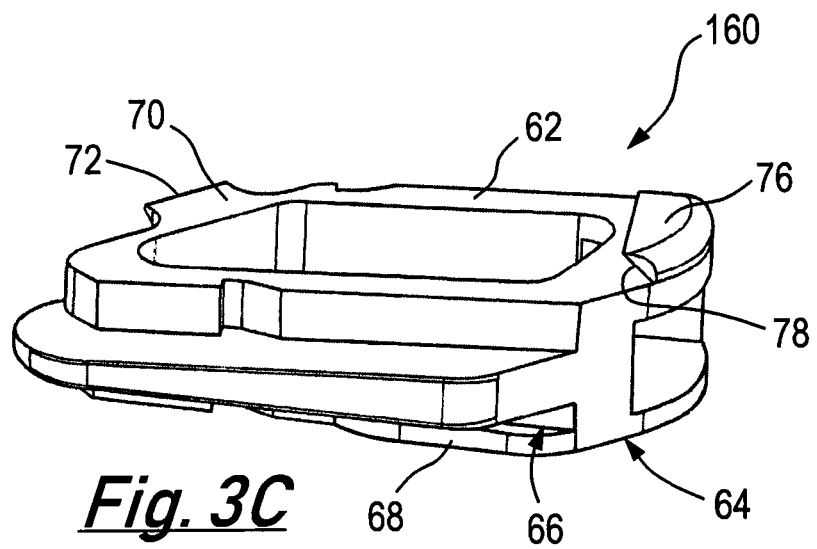
FIG. 3C shows core component of the third embodiment of the present invention.

A superior component, an inferior component and a core component of a first embodiment of intervertebral fusion device 10 are shown respectively in FIGS. 1A, 1B and 1C. The intervertebral fusion device 10 is an anterior lumbar interbody fusion (ALIF) device. FIG. 2A shows a core component before insertion between the superior and inferior components of FIGS. 1A and 1B according to a second embodiment of intervertebral fusion device with the second embodiment differing from the first embodiment in respect of the greater height of the core component of the second embodiment. FIG. 2B shows the core component of FIG. 2A after insertion between the superior and inferior components.

As mentioned above, the intervertebral fusion device 10 of FIGS. 1A to 2B comprises a superior component 20, an inferior component 40 and a core component 60, 80. Each of the superior component 20 and the inferior component 40 is generally of the form of a plate, albeit a plate having structures thereon and a large aperture therethrough. The core component 60, 80 has the form of a frustum of a wedge. As can be seen from comparison of FIG. 1C with FIGS. 2A and 2B, the core component of FIG. 1C is thinner than the core component of FIGS. 2A and 2B. What is shown in FIGS. 2A and 2B therefore constitutes a second embodiment. Use of core components of different thicknesses and/or different extents of tapering wedge and with the same superior component 20 and inferior component 40 provides for different heights and angles of intervertebral fusion device 10. When the intervertebral fusion device 10 is being brought into use, the superior component 20 and the inferior component 40 are placed in the intervertebral space. The core component 60, 80 is positioned relative to the superior component 20 and the inferior component 40 as shown in FIG. 2A. Then the core component 60, 80 is positioned between edges of the superior component 20 and the inferior component 40 with the thin edge of the core component foremost before the core component is progressively inserted between the superior component and the inferior component until fully received between the superior component and the inferior component. FIG. 2B shows the intervertebral fusion device 10 when the core component 60, 80 is fully received between the superior component 20 and the inferior component 40. When in the disposition shown in FIG. 2B, the superior component top side abuts against a first vertebra defining the intervertebral space in part and the inferior component bottom side abuts against a second vertebra defining the intervertebral space in part.

The superior component 20 will now be described further with reference to FIG. 1A. The superior component 20 has a superior component top side 22, a superior component bottom side 24, a first lateral side 26 and a second lateral side 28. The superior component 20 comprise a first superior component profile 30 and a second superior component profile 32. The first superior core profile 30 is on the first lateral side 26 and the second superior core profile 32 is on the second lateral side 28. The first superior component profile and the first superior core profile, which is described below, abut and the second superior component profile and the second superior core profile, which is described below, abut whereby there is substantially no movement of the core component 60, 80 relative to the superior component 20 in a direction transverse to the direction of insertion of the core component between the superior and inferior components.

The superior component 20 also has a superior component rear formation 34 which extends along a back edge of the superior component in a direction transverse to the direction of insertion of the core component, the back edge being opposite the edge at which the core component is first received upon insertion. The superior component rear formation 34 comprises a protrusion which defines an inclined surface 36. The superior component 20 also has a superior component front formation at an edge at which the core component is first received upon insertion of the core component. The superior component front formation comprises two recesses 38 which are spaced apart in the transverse direction. A surface of each recess 38 facing opposite the direction of insertion of the core component defines an inclined surface 39. The inclined surfaces 39 can be seen more clearly in FIG. 2A.

The inferior component 40 will now be described further with reference to FIG. 1B. The inferior component 40 has an inferior component top side 42, an inferior component bottom side 44, a first lateral side 46 and a second lateral side 48. The inferior component comprises a first inferior component formation 50 and a second inferior component formation 52. The first inferior component formation 50 is towards the first lateral side 46 and the second inferior component formation 52 is towards the second lateral side 48. The first and second inferior component formations 50, 52 oppose each other and are spaced apart in a direction transverse to the direction of insertion of the core component between the inferior and superior components. The core component 60, 80 is received between the first and second inferior component formations 50, 52 during insertion. Each of the first and second inferior component formations 50, 52 defines a groove 54 which extends from the edge of the inferior component 40 that first receives the core component 60, 80 when the core component is being inserted. The opening to the groove 54 faces in the transverse direction.

The inferior component 40 also comprises an inferior component rear formation 56 which extends along a back edge of the inferior component in a direction transverse to the direction of insertion of the core component, the back edge being opposite the edge at which the core component is first received upon insertion. The inferior component rear formation 56 defines an elongate protrusion which is spaced apart from the inferior component top side 42 and which extends in the opposite direction to the direction of insertion of the core component 60, 80. The inferior component 40 defines an elongate aperture 58 near the edge of the inferior component that first receives the core component 60, 80 during insertion. The elongate aperture 58 extends in the transverse direction and is located centrally between the first and second inferior component formations 50, 52.

The core component 60 will now be described further with reference to FIG. 1C. As described above, the core component 60 has the form of a frustum of a wedge. The core component 60 has an upper side 62 and a lower side 64, the core component 60 being configured to be inserted between the superior and inferior components 20, 40 such that the upper side 62 faces the superior component bottom side 24 and the lower side 64 faces the inferior component top side 42. The core component 60 has a first lateral side 66 and a second lateral side (not seen in FIG. 1C) which each face in a direction orthogonal to a direction of insertion of the core component and to a direction of separation of the inferior and superior components, with the first and second lateral sides facing in opposite directions. A first inferior core formation 68 is on the first lateral side 66 and a second inferior core formation (not seen in FIG. 1C) is on the second lateral side. The first and second inferior core formations are of the same albeit mirror image form as each other. Each of the first and second inferior core formations 68 defines an elongate protrusion which extends in the transverse direction and from about half way along the core component 60 from the edge of the core component first received between the inferior and superior components to the opposite edge of the core component.

The core component 60 also comprises a superior core rear formation 70 which extends adjacent the upper side 62 and along an edge of the core component which is first received between the inferior and superior components during insertion of the core component. The superior component rear formation 70 comprises a protrusion which defines an inclined surface 72 which faces obliquely away from the core component and down from the upper side 62. The core component 60 further comprises an inferior core rear formation 74 in the form of a protrusion which extends from the lower side 64 and along the edge of the core component which is first received between the inferior and superior components during insertion of the core component.

The core component 60 also comprises a superior core front formation towards an edge opposite the edge first received between the inferior and superior components during insertion of the core component. The superior core front formation comprises two protrusions 76. The two protrusions 76 extend up from the upper side 62 and are spaced apart from each other in the transverse direction. Each of the protrusions 76 defines an inclined surface 78 which faces obliquely down towards the upper side 62 and towards the edge first received between the inferior and superior components during insertion. The core component 60 further comprises in its lower side 64 a living hinge which defines a protrusion 79 thereon. Inherent spring bias of the living hinge urges the protrusion 79 towards the inferior component 40 when the core component 60 is received between the superior and inferior components 20, 40.

As described above, the superior and inferior components 20, 40 are placed in the intervertebral space and the core component 60, 80 is positioned relative to the superior and inferior components as shown in FIG. 2A before the core component is inserted between the superior and inferior components. On initial insertion, the core component is placed generally between the superior and inferior components. During further insertion the core component is moved towards the inferior component until each first inferior core formation 68 is received in its respective groove 54 to thereby present a barrier to separation of the core component from the inferior component in the direction of the superior component. Otherwise and upon the superior component being adjacent the core component, the first and second lateral sides 66 are snugly received between the first and second superior component profiles 30, 32 to guide their relative movement as the core component is progressively inserted whilst the superior component is free to move away from and towards the core component in the direction of separation of the inferior and superior components.

When the core component 60, 80 is approaching full insertion between the inferior and superior components 20, 40 the inferior core rear formation 74 is received under the inferior component rear formation 56 to thereby present a barrier to the edge of the core component lifting from the inferior component. At the same time, the superior core rear formation 70 starts to engage with the superior component rear formation 34 and the two protrusions 76 of the superior core front formation start to engage with the two recesses 38 of the superior component front formation. Considering the superior core rear formation 70 further, the inclined surface 72 of the superior core rear formation 70 slides over the inclined surface 36 of the superior component rear formation 34 to draw the core component and the superior component together at their respective edges. Considering the two protrusions 76 of the superior core front formation further, the inclined surfaces 78 of the protrusions 76 slide over the respective inclined surfaces 39 of the two recesses 38 of the superior component front formation to draw the core component and the superior component together at their respective edges.

When the core component 60, 80 is at full insertion, the protrusion 79 on the living hinge at the lower side 64 of the core component is urged by the inherent spring bias of the living hinge into the elongate aperture 58 in the inferior component. Reception of the protrusion 79 in the elongate aperture 58 presents a barrier to ejection of the core component from between the inferior and superior components.

Figure 4A:
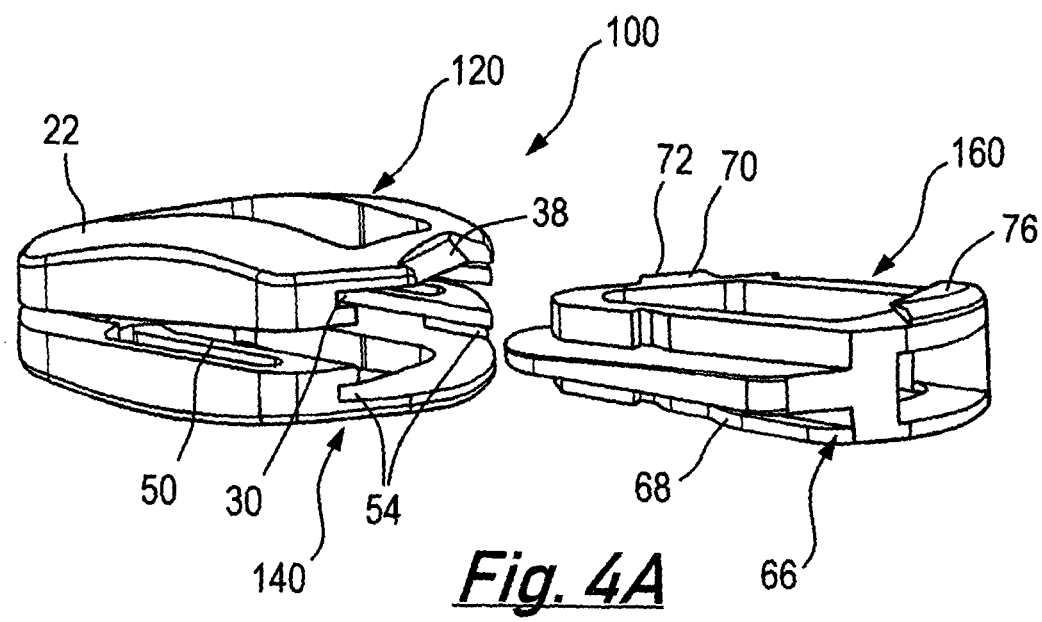
FIG. 4A shows the core component before insertion between the superior and inferior components according to the third embodiment.
Figure 4B:
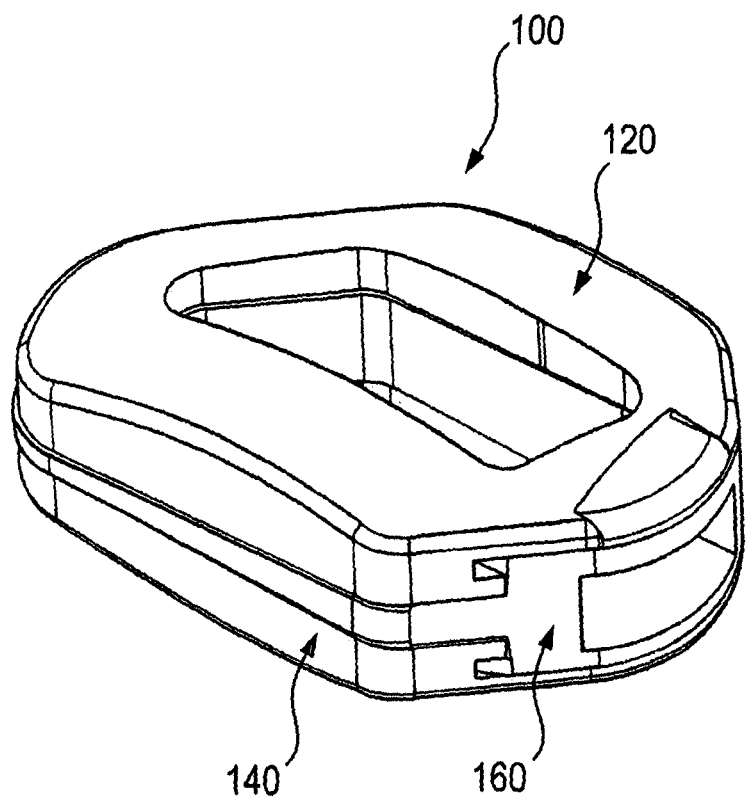
FIG. 4B shows the core component after insertion between the superior and inferior components according to the third embodiment.

A third embodiment of intervertebral fusion device 100 is shown in FIGS. 3A to 4B. The intervertebral fusion device 100 according to the third embodiment is an oblique lateral interbody fusion device. A superior component 120, an inferior component 140, and a core component 160 of the third embodiment are shown respectively in FIGS. 3A, 3B and 3C. FIG. 4A shows the core component 160 of the third embodiment before insertion between the superior and inferior components 120, 140 of FIGS. 3A and 3B. FIG. 4B shows the core component 160 of the third embodiment after insertion between the superior and inferior components 120, 140 of FIGS. 3A and 3B. The superior component 120, the inferior component 140, and the core component 160 of the third embodiment are of different shape and dimensions to the first and second embodiments when viewed in plan whereby the third embodiment is configured for insertion into an intervertebral space from an oblique lateral direction. Otherwise, and except as described below, the third embodiment is configured in respect of key features in the same fashion as the first and second embodiments. Such key features are therefore indicated in FIGS. 3A to 4B by the same reference numerals as for the first and second embodiments and the reader's attention is directed to the preceding description for a description of such key features. In respect of differences, as can be seen from FIG. 3C, the core component 160 has one anterior formation 76 on its upper side instead of the two anterior formations 76 of the first and second embodiments. Correspondingly, the superior component 120 of the third embodiment has one recess 38 at its anterior edge instead of the two recesses of the first and second embodiments. Furthermore, the third embodiment lacks the first and second embodiments' combination of the protrusion 79 on the living hinge in the core component and the elongate aperture 58 in the inferior component.

Figure 5:
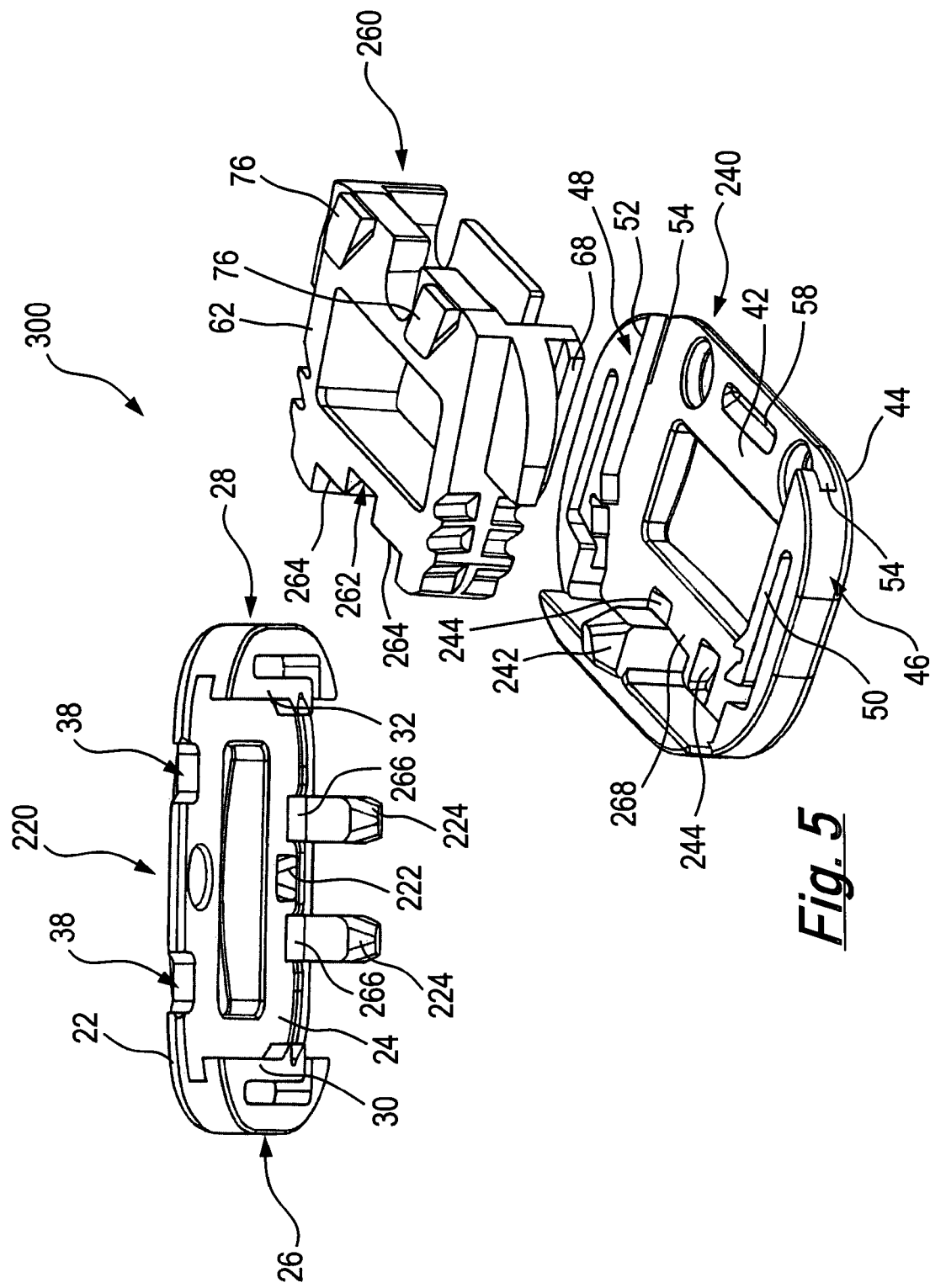
FIG. 5 shows an intervertebral fusion device according to a fourth embodiment.

A fourth embodiment of intervertebral fusion device 200 is shown in FIG. 5. The fourth embodiment 200 has a superior component 220, an inferior component 240, and a core component 260. The fourth embodiment 200 is an anterior lumbar interbody fusion (ALIF) device like the first and second embodiments. Except as described below, the third embodiment is configured in respect of key features in the same fashion as the first and second embodiments. Such key features are therefore indicated in FIG. 5 by the same reference numerals as for the first and second embodiments and the reader's attention is directed to the preceding description for a description of such key features.

In respect of differences, as can be seen from FIG. 5, the fourth embodiment 200 lacks the combination of the superior core rear formation 70 and the superior component rear formation 34 and also the combination of the inferior core rear formation 74 and the inferior component rear formation 56. Instead, the inferior component 240 of the fourth embodiment 200 has an upwardly extending post 242 near its posterior edge and an aperture 244 on each side of the upwardly extending post 242. The superior component 220 of the fourth embodiment 200 has an aperture 222 near its posterior edge and a downwardly extending post 224 on each side of the aperture 222. The core component 260 of the fourth embodiment 200 has a core recess 262 which is centrally located in a posterior wall of the core component at the upper side 62. The fourth embodiment 200 is brought into use by positioning the inferior and superior components 220, 240 in the intervertebral space and such that each of the downwardly extending posts 224 is received in a respective one of the two apertures 244 in the inferior component and such that the upwardly extending post 242 is received in the aperture 222 in the superior component 220. Relative movement of the inferior and superior components 220, 240 is thus restricted whilst rotation of an end of each of the downwardly and upwardly extending posts 224, 242 in its respective aperture 222, 244 allows for the inferior and superior components to rotate towards the posterior aspect in relation to each other. The core component 260 is then inserted between the inferior and superior components 220, 240. When the core component 260 is fully received between the inferior and superior components 220, 240, the side of the upwardly extending post 242 is received in the core recess 262. Furthermore, when the core component is fully received, a leading sharp edge 264 on each side of the core recess 262 and at the upper side 62 is received with a recess 266 defined towards the proximal end of a respective one of the two downwardly extending posts 224, to thereby present resistance to separation of the superior component 220 and the core component 260 from each other at the posterior aspect. The upwardly extending post 242 on the inferior component 240 defines a recess 268 towards its proximal end. A sharp edge (not seen in FIG. 5) at the lower side and the posterior aspect of the core component 260 is received in the recess 268 in the upwardly extending post 242 to thereby present resistance to separation of the inferior component 240 and the core component 260 from each other at the posterior aspect.

The invention claimed is:

1. An intervertebral fusion device comprising:
a superior component having a superior component top side and a superior component bottom side, the superior component configured to be received in an intervertebral space between first and second vertebrae whereby the superior component top side is configured to abut against the first vertebra, the superior component comprising a first superior component profile and a second superior component profile, the first and second superior component profiles located towards respective opposite edges of the superior component and facing each other;

an inferior component having an inferior component top side and an inferior component bottom side, the inferior component configured to be received in the intervertebral space between the first and second vertebrae whereby the inferior component bottom side is configured to abut against the second vertebra, the superior component bottom side and the inferior component top side opposing each other when the superior and inferior components are received in the intervertebral space; and a core component configured for insertion between the superior and inferior components whereby a separation between the superior and inferior components is determined when the intervertebral fusion device is in the intervertebral space, wherein the core component comprises an inferior core formation and the inferior component top side comprises an inferior component formation, one of the inferior core formation and the inferior component formation defines a groove and the other of the inferior core formation and the inferior component formation defines an elongate protrusion, the elongate protrusion shaped to be slidably received in the groove as the core component is progressively inserted between the superior and inferior components whereby the inferior core formation inter-engages with the inferior component formation to prevent separation of the core component and the inferior component from each other in the direction of separation of the superior and inferior components, the core component has first and second lateral faces which face in opposite directions, the first and second lateral faces snugly received between the first and second superior component profiles to guide relative movement of the core component and the superior component in the direction of insertion of the core component between the superior and inferior components whilst the superior component is free to move away from and towards the core component in the direction of separation of the superior and inferior components and as the core component is progressively inserted between the superior and inferior components, and the core component comprises a superior core formation and the superior component bottom side comprises a superior component formation, the superior core formation and the superior component formation inter-engaging with each other when the core component is substantially fully received between the superior and the inferior components following insertion of the core component between the superior and inferior components to thereby prevent separation of the core component and the superior component from each other in the direction of separation of the superior and inferior components.

2. The intervertebral fusion device according to claim 1, wherein the core component has an upper side and a lower side, the upper side facing the superior component bottom side and the lower side facing the inferior component top side when the core component is inserted between the inferior and superior components, and wherein the upper side and the lower side of the core component are inclined to each other whereby the core component has the form of a wedge.

3. The intervertebral fusion device according to claim 1, wherein the groove and the elongate protrusion extend between first and second oppositely directed sides of the intervertebral fusion device, the core component inserted between the superior and inferior components from the first side of the intervertebral fusion device.

4. The intervertebral fusion device according to claim 1, wherein the inferior component formation defines the groove and the inferior core formation defines the elongate protrusion.

5. The intervertebral fusion device according to claim 1, wherein the inferior core formation extends along the core component from a location on the core component spaced apart from an edge of the core component which leads insertion of the core component between the inferior and superior components.

6. The intervertebral fusion device according to claim 1, wherein the inferior component comprises first and second inferior component formations located towards respective opposite edges of the inferior component, wherein the core component comprises first and second inferior core formations spaced apart in a direction transverse to the direction of insertion of the core component between the inferior and superior components, and wherein the protrusion of one of the first inferior component formation and the first inferior core formation is slidably received in the groove of the other of the first inferior component formation and the first inferior core formation, and the protrusion of one of the second inferior component formation and the second inferior core formation is slidably received in the groove of the other of the second inferior component formation and the second inferior core formation as the core component is progressively inserted between the superior and inferior components.

7. The intervertebral fusion device according to claim 6, wherein the first and second inferior core formations are oppositely directed and each faces in the transverse direction, wherein the first and second inferior core formations face in opposite directions, and wherein the first inferior component formation and the first inferior core formation cooperate and the second inferior component formation and the second inferior core formation cooperate to limit movement in the transverse direction of the core component relative to the inferior component.

8. The intervertebral fusion device according to claim 1, wherein the first superior component profile and the first lateral face of the core component cooperate and the second superior component profile and the second lateral face of the core component cooperate to limit movement of the core component relative to the superior component in a direction transverse to the direction of insertion of the core component between the inferior and superior components.

9. The intervertebral fusion device according to claim 1, wherein the inferior component comprises an inferior component rear formation which extends along a rear of the inferior component in a direction transverse to the direction of insertion of the core component between the superior and inferior components from a front of the inferior component, wherein the core component comprises an inferior core rear formation which extends along an edge of the core component which is first received between the inferior and superior components when the core component is inserted between the superior and inferior components, and wherein the inferior component rear formation and the inferior core rear formation inter-engage when the core component is substantially fully received between the inferior and superior components to prevent separation of the core component and the inferior component from each other in the direction of separation of the superior and inferior components.

10. The intervertebral fusion device according to claim 1, wherein the superior component formation comprises a superior component rear formation extending along a rear of the superior component in a direction transverse to the direction of insertion of the core component between the superior and inferior components from a front of the superior component.

11. The intervertebral fusion device according to claim 10, wherein the superior core formation comprises a superior core rear formation extending along an edge of the core component which is first received between the inferior and superior components upon insertion of the core component between the superior and inferior components, and wherein the superior component rear formation and the superior core rear formation inter-engage when the core component is substantially fully inserted between the superior and inferior components to prevent separation of the core component and superior component from each other in the direction of separation of the superior and inferior components.

12. The intervertebral fusion device according to claim 11, wherein the superior component rear formation and the superior core rear formation are configured such that they start to engage with each other when the core component is at least 80% received between the inferior and superior components.

13. The intervertebral fusion device according to claim 1, wherein the superior component formation comprises a superior component front formation located towards an edge of the superior component at which the core component is first received upon insertion of the core component between the superior and inferior components.

14. The intervertebral fusion device according to claim 13, wherein the superior core formation comprises a superior core front formation located towards an edge of the core component opposite the edge of the core component first received between the inferior and superior components upon insertion of the core component, and wherein the superior component front formation and the superior core front formation inter-engage when the core component is substantially fully inserted to prevent separation of the core component and superior component in the direction of separation of the superior and inferior components.

15. The intervertebral fusion device according to claim 1, wherein the superior component, the inferior component and the core component are separate components, and wherein the superior component and the inferior component do not engage with each other other than by way of the core component.

16. The intervertebral fusion device according to claim 1 further comprising a locking arrangement, a first locking part of the locking arrangement comprised in the core component and a second locking part of the locking arrangement comprised in the inferior component, wherein the first locking part comprises a living hinge which defines a protrusion thereon and the second locking part defines an aperture, the living hinge urged by inherent spring bias in the direction of separation of the superior and inferior components such that the protrusion on the living hinge is received in the aperture of the second locking part whereby the first and second locking parts inter-engage to prevent ejection of the core component from between the inferior and superior components.

17. The intervertebral fusion device according to claim 1, wherein the first superior component profile and the first lateral face abut and are configured to slide over each other in the direction of separation of the inferior and superior components, and the second superior component profile and the second lateral face abut and are configured to slide over each other in the direction of separation of the inferior and superior components as the core component is inserted between the superior and inferior components.

18. The intervertebral fusion device according to claim 17, wherein at least one of the first superior component profile and the first lateral face is linear in the direction of separation of the superior and inferior components whereby the first superior component profile and the first lateral face slide over each other in the direction of separation of the inferior and superior components, and at least one of the second superior component profile and the second lateral face is linear in the direction of separation of the superior and inferior components whereby the second superior component profile and the second lateral face slide over each other in the direction of separation of the inferior and superior components.

19. The intervertebral fusion device according to claim 18, wherein each of the first and second lateral faces is linear in the direction of separation of the inferior and superior components along a whole length of the lateral face in the direction of insertion of the core component between the superior and inferior components.

20. The intervertebral fusion device according to claim 18, wherein the first and second lateral faces are substantially parallel with each other.

21. A method of installing an intervertebral fusion device in an intervertebral space between first and second adjacent vertebrae, the intervertebral fusion device comprising a superior component having a superior component top side and a superior component bottom side, an inferior component having an inferior component top side and an inferior component bottom side, and a core component, the method comprising:
positioning the superior component and the inferior component relative to each other such that the superior component bottom side and the inferior component top side oppose each other;
inserting the core component between the superior and inferior components whereby a separation between the superior and inferior components is determined; and
disposing the intervertebral fusion device in the intervertebral space such that the superior component top side abuts against the first vertebra and the inferior component bottom side abuts against the second vertebra,
wherein the superior component comprises a first superior component profile and a second superior component profile, the first and second superior component profiles located towards respective opposite edges of the superior component and facing each other,
wherein the core component comprises an inferior core formation and the inferior component top side comprises an inferior component formation, one of the inferior core formation and the inferior component formation defines a groove and the other of the inferior core formation and the inferior component formation defines an elongate protrusion, the elongate protrusion shaped to be slidably received in the groove as the core component is progressively inserted between the superior and inferior components whereby the inferior core formation inter-engages with the inferior component formation to prevent separation of the core component and the inferior component from each other in the direction of separation of the superior and inferior components,
wherein the core component has first and second lateral faces which face in opposite directions, the first and second lateral faces snugly received between the first and second superior component profiles to guide relative movement of the core component and the superior component in the direction of insertion of the core component between the superior and inferior components whilst the superior component is free to move away from and towards the core component in the direction of separation of the superior and inferior components and as the core component is progressively inserted between the superior and inferior components, and
wherein the core component comprises a superior core formation and the superior component bottom side comprises a superior component formation, the superior core formation and the superior component formation inter-engaging with each other when the core component is substantially fully received between the superior and the inferior components following insertion of the core component between the superior and inferior components to prevent separation of the core component and the superior component from each other in the direction of separation of the superior and inferior components.

22. The method of installing an intervertebral fusion device according to claim 21 wherein the superior and inferior components are positioned relative to each other in the intervertebral space before the core component is inserted between the superior and inferior components.

* * * * *